United States Patent [19]
Bis et al.

[11] Patent Number: 5,808,468
[45] Date of Patent: Sep. 15, 1998

[54] UNIVERSAL KINEMATIC IMAGING TABLE FOR RAPID POSITIONAL CHANGES IN PATIENT CENTERING

[76] Inventors: Kostaki G. Bis, 3642 Ridgeland Ct., W. Bloomfield, Mich. 48323; Anil N. Shetty, 4655 Bentley Dr., Troy, Mich. 48098

[21] Appl. No.: 766,289

[22] Filed: Dec. 13, 1996

[51] Int. Cl.$^6$ .................................................. A61B 5/055
[52] U.S. Cl. ........................ 324/318; 600/415; 600/420; 5/601; 5/943
[58] Field of Search ................................ 324/318; 5/600, 5/601; 378/208, 209; 600/415, 421, 420

[56] References Cited

U.S. PATENT DOCUMENTS

| | | | |
|---|---|---|---|
| 4,727,328 | 2/1988 | Carper et al. ........................... | 324/318 |
| 4,771,785 | 9/1988 | Duer ....................................... | 600/415 |
| 4,944,501 | 7/1990 | Sireul et al. ............................. | 5/601 |
| 5,197,474 | 3/1993 | Englund et al. ........................ | 600/415 |
| 5,199,123 | 4/1993 | Jacques et al. . | |
| 5,398,686 | 3/1995 | Inoue et al. ............................. | 600/425 |
| 5,490,508 | 2/1996 | Kato ........................................ | 600/422 |
| 5,590,429 | 1/1997 | Boomgaarden et al. ................ | 5/600 |

*Primary Examiner*—Sandra L. O'Shea
*Assistant Examiner*—Michael Eisenberg
*Attorney, Agent, or Firm*—Harness, Dickey & Pierce, P.L.C.

[57] ABSTRACT

An examination table for use with an imaging device is provided with a rolling track on an upper surface of a platform. A table is supported on the rolling track for movement relative to the platform. The imaging machine includes lower coils which are supported under the table and upper coils which are supported on the platform. The table and the rolling track are made from a non-ferromagnetic material so as not to interfere with the coils. The examination table can also be used with other imaging machines such as computed tomography and x-ray machines.

9 Claims, 4 Drawing Sheets

UNIVERSAL KINEMATIC IMAGING TABLE FOR RAPID POSITIONAL CHANGES IN PATIENT CENTERING

BACKGROUND OF THE INVENTION

FIELD OF THE INVENTION

The present invention relates to a kinematic imaging table, and more particularly, to a kinematic imaging table for rapid positional changes in patient centering for use with a magnetic resonance imaging (MRI) machine, a computed tomography (CT) imaging device, or other imagery systems including x-ray units.

BACKGROUND AND SUMMARY OF THE INVENTION

The use of imagery systems like magnetic resonance imaging and computed tomography imaging is well known in the medical field. A patient going through such examinations typically must lie flat on an examination table which is inserted into the imaging device. The patient is required to lie still for extended periods of time in order to obtain accurate data from the imaging device. For MRI devices, there are generally two types of coils which are used, body coils and surface coils. Body coils are mounted around the gantry in the body of the MRI device. Body coils generally suffer from the disadvantage that they do not provide the desired signal-to-noise ratio and spatial resolution. Surface coils provide superior spatial resolution and signal as compared to body coils. Surface coils are utilized by placing a posterior coil in the form of a circular or rectangular plate which houses the coil on a table underneath a patient. An anterior coil, also in the form of a circular or rectangular plate which houses the coil is strapped to the patient's frontal region. The anterior coil is disposed above the posterior coil. The posterior and anterior coils are provided in the area of the body which is being imaged. Typically, when different areas of the patient are to be examined, the coils used for creating the images must be moved relative to the patient's body. The delay in moving the coils contributes to the time necessary for obtaining the necessary images, thus, contributing to the patient's discomfort and overall examination time. Furthermore, in the imagery of, for example, blood vessels, a control material is injected into the patient's blood stream. As the control material is circulated through the blood vessels, it is necessary for the patient to be moved relative to the imaging coils in order to obtain an accurate image of the blood vessels. Because the contrast is only effective for limited periods of time, the time required for moving the surface coils is prohibitive for imaging blood vessels in different anatomic locations.

In the case of an MRI device utilizing body coils, the bed on which the patient is on can be moved relative to the body coils. However, the body coils do not provide the desired spatial resolution and signal for obtaining clear images. Furthermore, current table speeds are not sufficient for rapid positional changes of patient centering. Therefore, x-ray angiography remains the predominant method of imaging blood vessels. However, x-ray angiography suffers from the drawbacks that it is invasive upon the patient due to the fact that it requires insertion of catheter devices into the patient's arteries or veins. These catheters are subsequently injected with contrast which leads to vascular opacification. Furthermore, x-ray angiography is expensive and time consuming. Therefore, it is desirable in the art of radiology to provide an imaging device which provides high resolution images and which permits rapid positional changes in patient centering so that the time required for obtaining accurate images of a patient may be reduced and so that movement of the patient relative to the imaging coils is simplified.

Accordingly, the present invention provides a magnetic resonance imaging device including an examination table movably supported on a track. A lower surface coil is supported under the table, and an upper surface coil is supported above the table. The table is movable relative to the upper and lower surface coils.

According to another aspect of the present invention, an examination table is provided for use with an imaging machine. The table includes a platform having a rolling track disposed on an upper surface t hereof. An examination table is movably mounted on the rolling track for supporting a patient thereon.

According to yet another aspect of the present invention, a method is provided for retrofitting an existing imaging device with an examination table according to the present invention.

The present invention provides a kinematic imaging table which allows rapid positional change in the patient centering in order to facilitate the imaging of blood vessels, in order to facilitate easy moving of the patient relative to the imaging coils, and to reduce the time required for obtaining the necessary images for a medical imaging examination.

Further areas of applicability of the present invention will become apparent from the detailed description provided hereinafter. It should be understood however that the detailed description and specific examples, while indicating preferred embodiments of the invention, are intended for purposes of illustration only, since various changes and modifications within the spirit and scope of the invention will become apparent to those skilled in the art from this detailed description.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
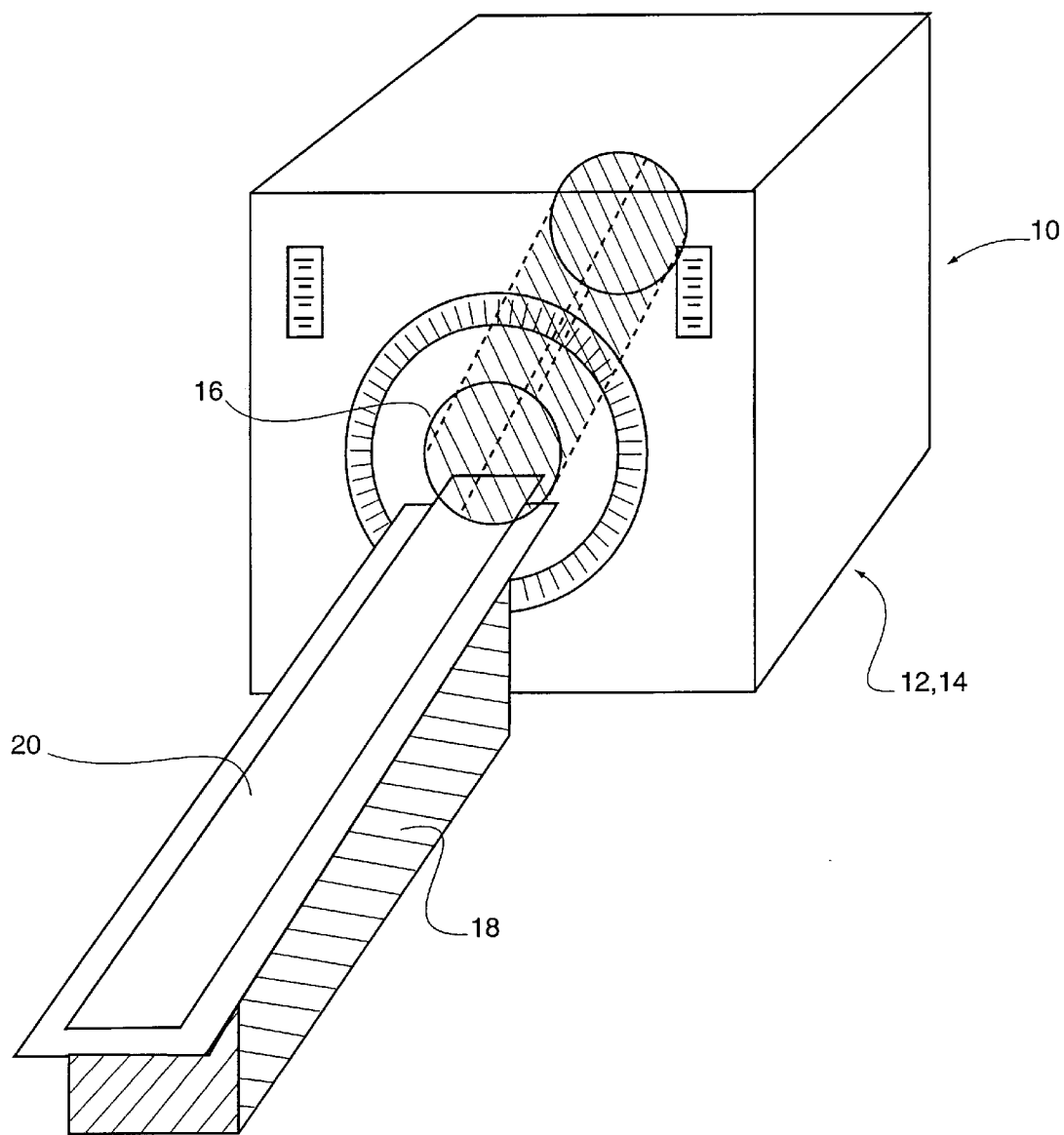
FIG. 1 is a general schematic view of a CT and a MRI imaging device.

The present invention relates to a universal kinematic imaging table for rapid positional changes in patient centering. In particular, the kinematic imaging table is used in conjunction with a magnetic resonance imaging and/or computed tomography imaging device 10. As shown in FIG.

1, the imaging device 10 generally includes a computed tomograph gantry 12 or a magnetic resonance imaging gantry 14. The computed tomography gantry and magnetic resonance imaging gantry each include a tunnel 16 for receiving a patient therein. A platform 18 is provided for supporting an examination table 20 which is received in the tunnel 16 of the imaging device 10.

Figure 2:
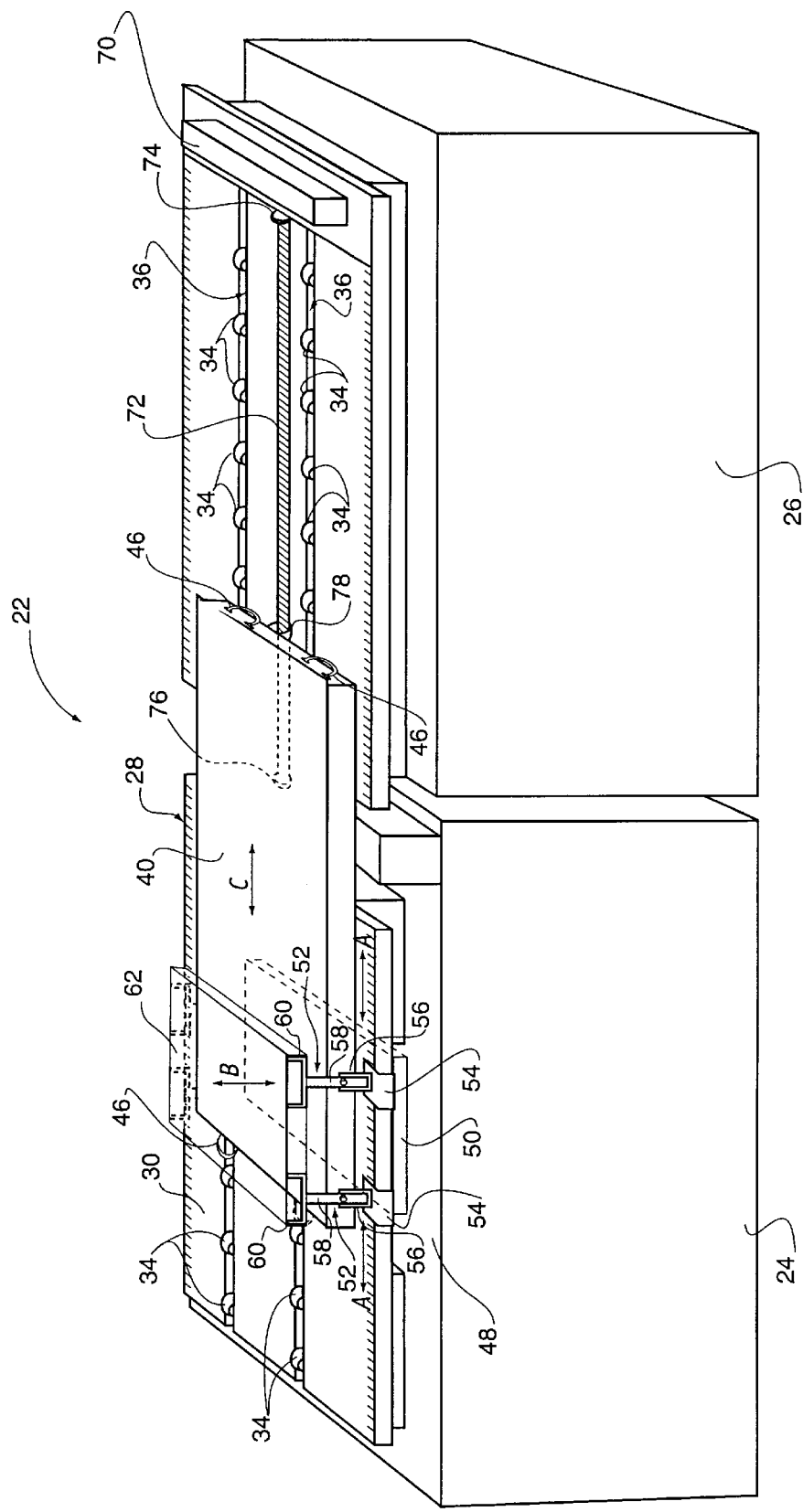
FIG. 2 is a perspective view of the universal kinematic imaging table according to the principles of the present invention.
Figure 3:
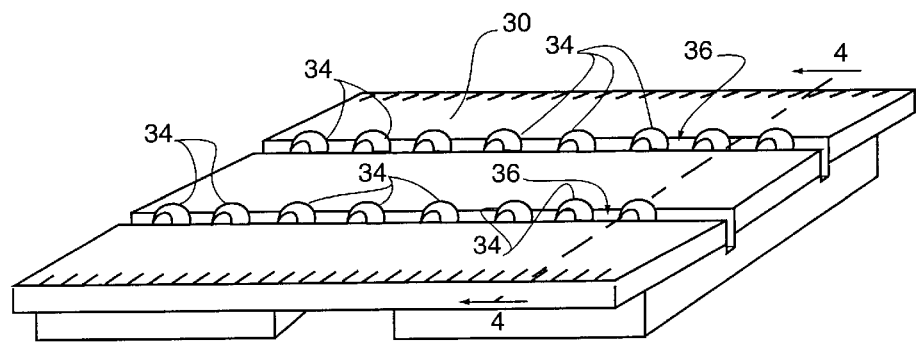
FIG. 3 is a perspective view of a platform having a rolling track according to the principles of the present invention.

According to the principles of the present invention, a kinematic imaging table is provided for rapid positional changes in patient centering, as shown in FIG. 2.

Figure 4:
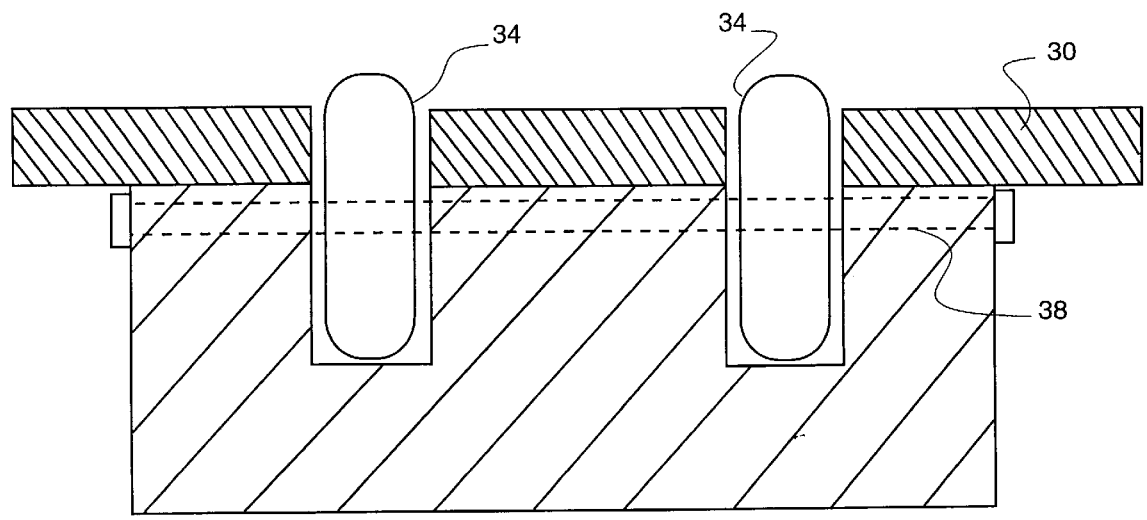
FIG. 4 is a sectional view taken along line 4—4 of FIG. 3.
Figure 5:
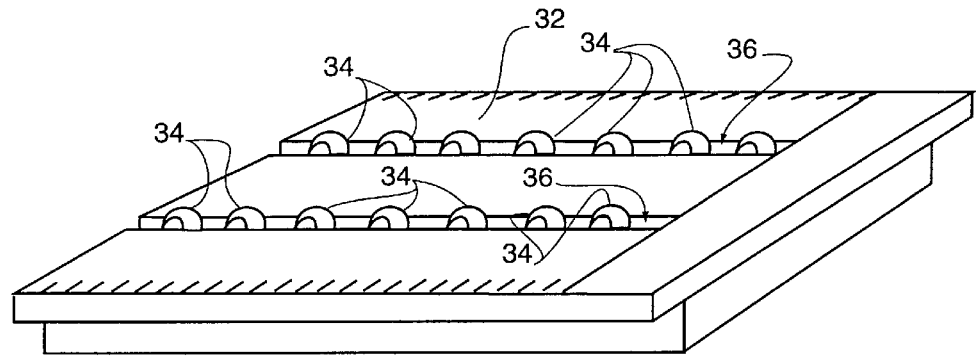
FIG. 5 is a perspective view of a second platform section having a rolling track disposed on an upper surface thereof.
Figure 6:
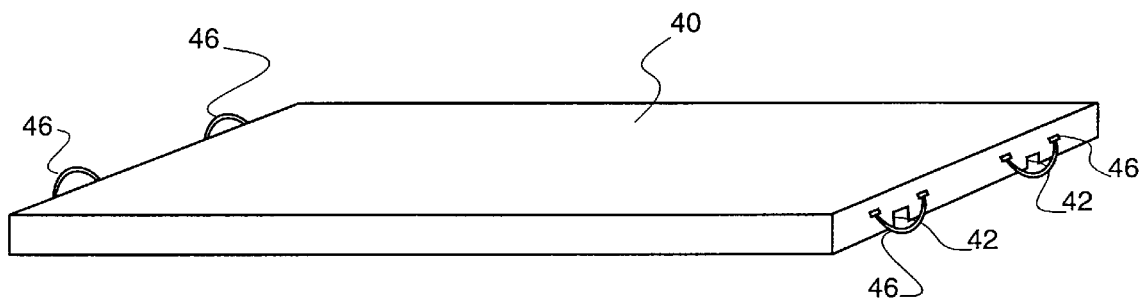
FIG. 6 is a perspective view of a movable table according to the principles of the present invention.
Figure 7:
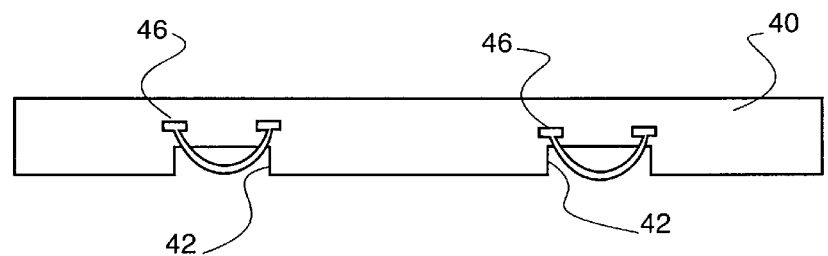
FIG. 7 is an end view of the movable table shown in FIG. 6.

With reference to FIG. 2, the imaging table 20 of the present invention is shown in combination with existing imaging and outer tables 24, 26, respectively. The kinematic imaging table 22 of the present invention includes a base platform 28 including a first platform portion 30 and a second platform portion 32. The first platform portion 30 is disposed on the existing imaging table 24. The second platform portion 32 is provided on the existing outer table 26. Outer table 26 may be provided with vertical adjustment capabilities for raising and lowering second platform portion 32. First and second platform portions 30, 32 are provided with a plurality of rollers 34 arranged in a pair of columns 36. Rollers 34 are supported by rods 38, as shown in FIG. 4. Rollers 34 and rods 38 are preferably made from a non-ferrous material such as plastic.

An examination table 40 is supported on the plurality of rollers 34. Examination table 40 is provided with grooves 42 extending longitudinally along a lower surface 44 thereof. Examination table 40 can be provided with handles 46 disposed on the ends or sides of the table 40. Examination table 40 is preferably made from a non-ferrous material such as plastic or wood.

An area beneath the first platform portion 30 is provided an opening which defines a space 48 for receiving a lower or posterior surface coil 50 therein. The posterior surface coil 50 is provided in the form of a rectangular plate which contains the coils therein. A pair of movable support members 52 are disposed on each side of the first platform portion 30. The support members 52 include C-clamps 54 which attach to the platform 30 and are adjustable in the longitudinal direction as shown by arrows A. The support member 52 further includes a vertically-extending post 56 and an adjustable slide member 58 having a coil-supporting bracket 60 disposed at an upper portion thereof. The slide members are adjustable relative to posts 56 as shown by arrows B. An anterior or upper surface coil 62 is supported on the brackets 60 of support members 52. The upper surface coil 62 is disposed directly above lower surface coil 50.

In operation, the examination table 40 is disposed on the second platform portion 32 on outer table 26. A patient is placed on the examination table 40 and the table is rolled onto the first platform portion 30 and positioned such that the portion of the patient which is desired to be imaged is located between the upper and lower coils 62, 50. During the imaging process, the patient can be moved relative to the upper and lower coils 62, 50 by a technician who will use the handles 46 for moving the table. Alternatively, a motor 70 can be utilized for automatically adjusting the position of the examination table 40. Motor 70 is provided with a forward and reverse operating mode and has an output shaft attached to a screw device 72 which is supported by bearings 74, 76. Screw device 72 engages a nut 78 attached to examination table 40. The rotation of screw 72 causes nut 78 to travel along the axis of the screw 72, thereby moving the examination table 40 in the longitudinal direction as indicated by arrows C. Reversal of the motor 70 causes the screw device 72 to drive in the opposite direction, thereby causing the examination table 40 to move in the opposite direction.

In the invention disclosed above, the examination table 40 and rollers 34 may be placed wider apart so that the posterior coil can be placed directly beneath the examination table between the columns 36 of rollers 34. Furthermore, the rollers 34 may also be provided on the bottom of the examination table 40 while the first and second platform portions would then be provided with a track for receiving the rollers. It should be understood that other known track devices can be utilized for slidably supporting the examination table on the base platform.

The kinematic imaging table of the present invention allows for the use of surface coils of an MRI machine for use in rapidly imaging different body locations including blood vessels and could therefore replace the predominant technique of x-ray angiography which is invasive, expensive and time consuming. The kinematic imaging table can also be employed for rapid positional changes of patient centering when conducting computed tomography examinations and other imaging studies which utilize x-rays.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of retrofitting an existing imaging device having a gantry and an existing imaging table with a kinematic examination table for rapid positional changes in patient centering for obtaining a series of images from an injection of contrast material, said imaging device including one of body coils or surface coils fixedly mounted relative to said gantry, comprising the steps of:

placing a base platform on said existing imaging table of said imaging device, said base platform including a first track portion;

providing a table made of a non-ferrous material on said base platform, said table including a second track portion for mating with said first track portion;

wherein said table is rapidly movable relative to said base platform and said gantry such that, during operation of said imaging device, said table is movable relative to said gantry to allow a patient to be repositioned within said gantry to allow a series of images to be taken of a patient's body as a contrast material, injected into the patient's body is circulated through the patient's blood vessels whereby the patient is movable relative to said one of said body coils or said surface coils.

2. The method according to claim 1, wherein one of said first and second track portions include a series of rollers and the other of said first and second track portions include at least one rail member for engaging said series of rollers.

3. The method according to claim 1, wherein said base platform includes a fist portion disposed in said gantry of said imaging device and a second portion disposed on a vertically movable platform of the existing imaging device, wherein said first track portion is disposed on each of said first and second portions of said base platform.

4. The method according to claim 1, wherein said base platform includes a space for receiving a surface coil under said table.

5. A retrofit examination table for use with an existing magnetic resonance imaging device including a gantry for receiving a patient therein and an existing imaging table for supporting a patient within said gantry, said retrofit examination table comprising:

a base portion which in use, is placed on said existing imaging table;

an examination table movably supported on said base portion for rapid positioning relative thereto such that during operation of said magnetic resonance imaging device the examination table is movable relative to said base portion to allow a patient to be repositioned within said gantry to allow a series of images to be taken of a patient's body as a contrast material injected into the patient's body is circulated through the patient's blood vessels.

6. The retrofit examination table according to claim 5, wherein said base portion and said examination table are made from a non-ferrous material.

7. The retrofit examination table according to claim 5, wherein said base portion includes a plurality of rollers disposed thereon for supporting said examination table.

8. The retrofit examination table according to claim 5, wherein said base portion defines a space for receiving a surface coil under said examination table.

9. The retrofit examination table according to claim 5, further comprising a support device; for supporting a surface coil above said table.

* * * * *